United States Patent [19]

Killian

[11] Patent Number: 5,534,548
[45] Date of Patent: Jul. 9, 1996

[54] METHOD OF TREATING PREECLAMPSIA

[75] Inventor: Anthony Killian, Libertyville, Ill.

[73] Assignee: TAP Pharmaceuticals, Inc., Deerfield, Ill.

[21] Appl. No.: 237,075

[22] Filed: May 3, 1994

[51] Int. Cl.$^6$ .......................... C07C 50/02; A61K 31/235
[52] U.S. Cl. .......................... 514/545; 514/570; 552/310
[58] Field of Search .................. 552/310; 514/545, 514/570

[56] References Cited

U.S. PATENT DOCUMENTS

| | | | |
|---|---|---|---|
| 4,808,627 | 2/1989 | Ogletree | 514/469 |
| 5,015,648 | 5/1991 | Humphrey | 514/317 |
| 5,180,742 | 1/1993 | Terao et al. | 514/558 |

OTHER PUBLICATIONS

S. W. Walsh et al., *Am. J. Obstetrics & Gyn.*, 169(6):1462–1465 (1993).
Y. Imura, *Japanese J. Pharmacol.*, 52(1):35–43 (1990).
G. Remuzzi, et al., *Am. J. Kidney Diseases*, 18(3):285–305 (1991).

*Primary Examiner*—Sharon A. Gibson
*Assistant Examiner*—Catherine Kilby Scalzo
*Attorney, Agent, or Firm*—Jerry F. Janssen

[57] ABSTRACT

Straight-chain alkanoic acids, substituted at the Ω-carbon atom by a substituted phenyl, naphthyl, furyl, or thienyl group and by a substituted 1,4-benzoquinon-2-yl group are effective in the therapy or prophylaxis of conditions associated with lipid peroxide injury to vascular endothelium particularly preeclampsia and eclampsia in pregnant females.

4 Claims, 10 Drawing Sheets

METHOD OF TREATING PREECLAMPSIA

TECHNICAL FIELD

The present invention relates to medical methods of treatment. More particularly, the present invention concerns the use of a class of substituted Ω-(1,4-benzoquinon-2-yl)alkanoic acids for the therapy or prophylaxis of conditions associated with excess production of lipid peroxides which may lead to vascular endothelial injury, particularly the conditions of preeclampsia and eclampsia.

BACKGROUND OF THE INVENTION

Preeclampsia is the development of hypertension with proteinuria or edema in pregnant women between the twentieth week of pregnancy and the end of the first week following delivery without apparent cause. Preeclampsia develops in roughly 5% of pregnant women, typically in women with a prior history of hypertension or vascular disease. If left untreated, preeclampsia can often rapidly progress to eclampsia which is fatal if untreated and which occurs in about 1 out of every 200 women who develop preeclampsia.

Mild preeclampsia is typically treated with bed rest. If the condition persists or develops into eclampsia, the usual treatment is the immediate induction of labor and delivery of the fetus.

In patients at high risk for the development of preeclampsia, low-dose aspirin therapy has also been tried as a preventative measure, but the data on the results are mixed. U.S. Pat. No. 5,015,648 discloses the use of (1R-(1α(Z),2β, 3β,5α))-(+)-7-(5-((1,1'-biphenyl)-4-yl)methoxy-3-hydroxy-2-(1-piperidinyl)cyclopentyl)-4-heptenoic acid or one of its physiologically acceptable salts for the therapy or prophylaxis of conditions associated with vasoconstriction and/or platelet aggregation in the uteroplacental circulation and/or excessive synthesis of thromboxane $A_2$ in the pregnant female subject.

SUMMARY OF THE INVENTION

The present invention, in its broadest aspect, provides a method for the use of a class of compounds having the structural formula I below for the therapy or prophylaxis of conditions associated with lipid peroxide injury to vascular endothelium as seen in microangiopathic anemias, including hemolytic uremic syndrome, thrombotic thrombocytopenic purpura and preeclampsia. The method comprises administering to a patient in need of such treatment a therapeutically effective amount of of a compound having the structural formula I:

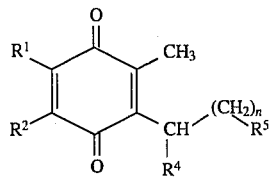

wherein n is an integer of 2 to 10, inclusive and $R^1$ and $R^2$ are independency selected from the group consisting of methyl or methoxy. Alternatively, $R^1$ and $R^2$ taken together are —CH=CH=CH=CH—.

In the structural formula above, $R^4$ is selected from the group consisting of phenyl, naphthyl, furyl, and thienyl, each of which is unsubstituted or substituted with one or more substituents selected from the group consisting of hydroxy, halogen, alkyl of one to three carbon atoms, alkoxy of one to three carbon atoms, acetyl, phenyl, p-tolyl, and m-tolyl.

The group $R^5$ is selected from the group consisting of carboxyl, alkoxycarbonyl of two to five carbon atoms, and phenoxycarbonyl; or a pharmaceutically acceptable salt thereof.

The compounds have been found to be particularly useful in the treatment of preeclampsia.

BRIEF DESCRIPTION OF THE DRAWING

In the drawing figures which form a part of the description of the present invention.

DETAILED DESCRIPTION AND PREFERRED EMBODIMENTS

Figure 1:
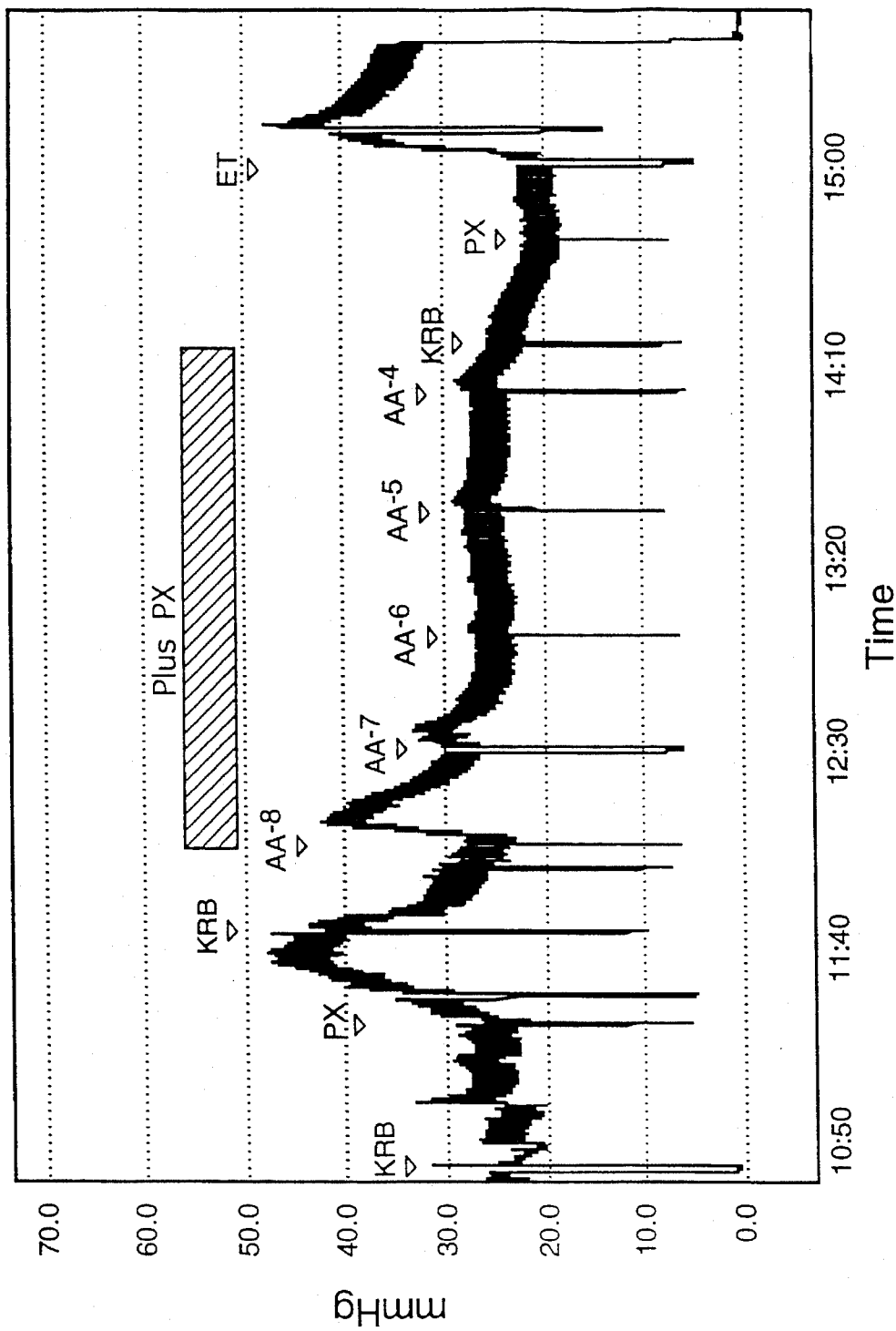
FIG. 1 shows a representative tracing of the changes in perfusion pressure in the isolated human placental cotyledon in response to peroxide perfusion and perfusion of peroxide in the presence of increasing concentrations of 7-(3,5,6-trimethyl-1,4-benzoquinon-2-yl)-7-phenylheptanoic acid.

The preparation of the compounds suitable in the medical method of treatment of the present invention and their use as agents for inhibiting the formation of lipid peroxides, as thromboxane $A_2$ antagonists, and as inhibitors of 5-lipoxygenase in the treatment of asthma, allergy and cerebral-circulatory metabolism are described in U.S. Pat. No. 5,180,742 which is incorporated herein by reference.

The class of compounds described there, particularly those of structural formula I above wherein $R^1$ and $R^2$ are methyl; and $R^4$ is selected from the group consisting of phenyl, optionally substituted with one or more substituents selected from alkyl of one to three carbon atoms, alkoxy of one to three carbon atoms, and halogen, and their pharmaceutically acceptable salts, are preferred.

Particularly preferred compounds for use in the method of treatment of this invention are compounds selected from the group consisting of:

7-(3,5,6-trimethyl- 1,4-benzoquinon-2-yl)-7-phenylheptanoic acid, 6-(3,5,6-trimethyl- 1,4-benzoquinon-2-yl)-6-(4-methoxyphenyl)hexanoic acid, 7-(3,5,6-trimethyl- 1,4-benzoquinon-2-yl)-7-(4-methoxyphenyl)heptanoic acid, 7-(3,5,6-trimethyl- 1,4-benzoquinon-2-yl)-7-(4-fluorophenyl)heptanoic acid, and 7-(3,5,6-trimethyl- 1,4-benzoquinon-2-yl)-7-(4-methylphenyl)heptanoic acid;

or a pharmaceutically acceptable salt thereof.

Most preferred among the specific compounds listed above is 7-(3,5,6-trimethyl-1,4-benzoquinon- 2-yl)-7-phenylheptanoic acid and its pharmaceutically acceptable salts.

By "pharmaceutically acceptable salt" it is meant those salts which are, within the scope of sound medical judgement, suitable for use in contact with the tissues of humans end lower animals without undue toxicity, irritation, allergic response and the like, and are commensurate with a reasonable benefit/risk ratio. Pharmaceutically acceptable salts are well known in the art. For example, S. M Berge, et al. describe pharmaceutically acceptable salts in detail in *J. Pharmaceutical Sciences*, 1977, 66:1–19. The salts can be prepared in situ during the final isolation and purification of the compounds of the invention, or separately by reacting the free acid function with a suitable organic or inorganic base. Representative salts include those of compounds of this invention with sodium, lithium, potassium, calcium, magnesium, and the like, as well as nontoxic ammonium, quaternary ammonium, and an-fine cations, including, but not limited to ammonium, tetramethylammonium, tetraethylammonium, methylamine, dimethylamine, trimethylamine, triethylamine, ethylamine, and the like.

Pharmaceutical compositions which may be employed in the method of this invention comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), buccally, or as an oral or nasal spray. The term "parenteral" administration as used herein refers to modes of administration which include intravenous, intramuscular, intraperitoneal, intracisternal, subcutaneous and intraarticular injection and infusion.

Pharmaceutical compositions of this invention for parenteral injection comprise pharmaceutically acceptable sterile aqueous or nonauueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oml), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drag form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable nonirritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and by gradually increase the dosage until the desired effect is achieved.

Generally dosage levels of about 25 to about 250 mg/day, preferably about 50 to about 150 mg per day of active compound are administered to a mammalian patient. If desired, the effective daily dose may be divided into multiple doses for purposes of administration, e.g. two to four separate doses per day.

In the following Examples, a representative compound of the class defined by Structure I above, namely 7-(3,5,6-trimethyl-1,4-benzoquinon-2-yl)-7-phenylheptanoic acid, was tested in an ex vivo model to test its ability to prevent peroxide induced vasoconstriction and to limit placental production of lipid peroxides.

Materials and Methods

Placentas were obtained immediately after term delivery from normally pregnant women.

Isolated Perfused Placental Cotyledon Methodology

This methodology was used as previously described S. W. Walsh, *Am. J. Obstet. Gynecol.*, 169: 1426–1466, 1993; J. A. Thorp, *Am. J. Obstet. Gynecol.*, 159: 1376–1380, (1988)). Briefly, a chorionic plate artery leading to a single placental cotyledon and a chorionic plate vein draining the cotyledon were catheterized and perfusion was begun immediately. Krebs-Ringer-bicarbonate (KRB) buffer gassed with 95% $O_2$, 5% $CO_2$ and warmed to 37° C. was used for perfusion. The placenta was placed in a water jacketed perfusion chamber warmed to 37° C. by a Haake constant-temperature circulating water bath (Haake model DIL, Fisher Scientific Co., Pittsburgh, Pa.). To continuously monitor the perfusion pressure, the fetal arterial catheter was connected to a pressure transducer connected to a Transbridge TBM 4 transducer amplifier connected to a MP10OWS data acquisition workstation (World Precision Instruments, Inc., Sarasota, Fla.). A Macintosh IIsi computer was used with Acq-Knowledge waveform data analysis software (World Precision Instruments, Inc., Sarasota, Fla.). The fetal side of the cotyledon was perfused at a rate of 3–4 ml/min to adjust the starting fetal side perfusion pressure to approximately 30 mm Hg. The intervillous space on the maternal side of the cotyledon was perfused at a rate of 8–10 ml/min by placing a butterfly needle attached to a catheter underneath the basal plate. Two Masterflex multichannel pumps were used for perfusion (Cole-Palmer Instrument Co., Chicago, Ill.). The pH, $pO_2$ and $pCO_2$ of the inflow and outflow lines were continuously monitored by Lazar Model PFS Perfusion Monitoring Systems with flow-through electrodes (Lazar Research Labs, Inc., Los Angeles, Calif.). Oxygen consumption and carbon dioxide production were calculated for each experiment to verify viability of the placental cotyledon. Following each experiment Crystal Violet dye was injected into the fetal arterial catheter in order to verify the cotyledon that was perfused; the cotyledon was then dissected fi-ee and weighed.

Sample Analysis;

Lipid peroiddes were analyzed by the spectrophotometric method specific for peroxides described by J. E. Frew, et al., in *Anal. Chim, Acta,* 155:139–150 (1983).. Hydrogen peroxide was used to generate the standard curve so the data are expressed as $H_2O_2$ equivalents. Thromboxane and prostacyclin were estimated by specific RIAs of their stable metabolites, $TXB_2$ and 6-keto $PGF_1\alpha$. Both assays were validated for analysis of the placental perfusion samples.

Calculations:

Placental secretion rates were calculated by multiplying the concentrations in either the fetal or maternal effluents by their respective effluent perfusion flow rates. Placental vascular resistance was calculated by dividing the chorionic plate arteriovenous pressure difference by the fetal effluent flow rate.

Satistical Analysis:

Data were analyzed by ANOVA (Randomized Complete Block) and Duncan New Multiple Range post-hoc test. A statistical computer software program was used (SuperANOVA, Abacus Concepts, Inc., Berkeley, Calif.). Log (X+1) transformation was used when the variances were not equal. A probability level of $P<0.05$ was considered significant.

EXAMPLE 1

Concentration Response of 7-(3,5,6-Trimethyl- 1,4-benzoquinon-2-yl)-7-phenylheptanoic Acid Placental cotyledons (n=5) were perfused serially for 20 minute intervals with control KRB buffer, t-butyl hydroperoxide (100 μM), control KRB buffer, and KRB buffer containing t-butyl hydroperoxide (100 μM) to which progressively increasing concentrations of 7-(3,5,6-trimethyl-1,4-benzoquinon-2-yl)-7-phenylheptanoic acid ($1\times10^{-8}$, $1\times10^{-7}$, $1\times10^{-6}$, $1\times10^{-5}$, and $1\times10^{-4}$ M) were added. Reagents were purchased from Sigma Chemical Co., St. Louis, Mo. t-Butyl hydroperoxide was used to stimulate endogenous production of lipid peroxides by stimulating the PGH synthase enzyme.

Peroxides are known to stimulate the activity of the cyclooxygenase component of PGH synthase. When PGH synthase is activated, the peroxidase function of the enzyme generates oxygen radicals that interact with polyunsaturated fatty acids in the placenta to form lipid peroxides.

Maternal and fetal effluent samples were collected during the last 10 minutes of each perfusion period and the effluent flow rates were recorded. Five ml of each sample was evaporated under vacuum centrifugation (SpeedVac Concentrator, Savant Instruments, Inc., Farmingdale, N.Y.) and then reconstituted with ultra pure water to 500 μL. t-Butyl hydroperoxide is a low molecular weight molecule that is evaporated by vacuum centrifugation. Therefore, the t-butyl hydroperoxide perfused in the experiment was not a contaminant of the concentrated samples and did not influence the measurement of the lipid peroxides.

The results of these tests are presented in FIGS. 1-5. FIG. 1 shows a representative tracing of the changes in perfusion pressure in response to peroxide perfusion and peroxide perfusion plus increasing concentrations of 7-(3,5,6-trimethyl-1,4-benzoquinon- 2-yl)-7-phenylheptanoic acid (AA). Perfusion pressure was substantially increased by the peroxide (PX) alone, but the increase in pressure was inhibited in a concentration response manner by 7-(3,5,6-trimethyl-1,4-benzoquinon-2-yl)-7-phenylheptanoic acid.

Peroxide alone was perfused again towards the end of the experiment without an increase in pressure demonstrating that the effect of 7-(3,5,6-trimethyl-1,4-benzoquinon-2-yl)-7-phenylheptanoic acid persisted after its perfusion was discontinued. However, when endothehn (ET, 40 nM) (a compound that vasoconstricts independent of thromboxane) was perfused, perfusion pressure increased demonstrating that the tissue was viable and capable of vasoconstriction.

Figure 2:
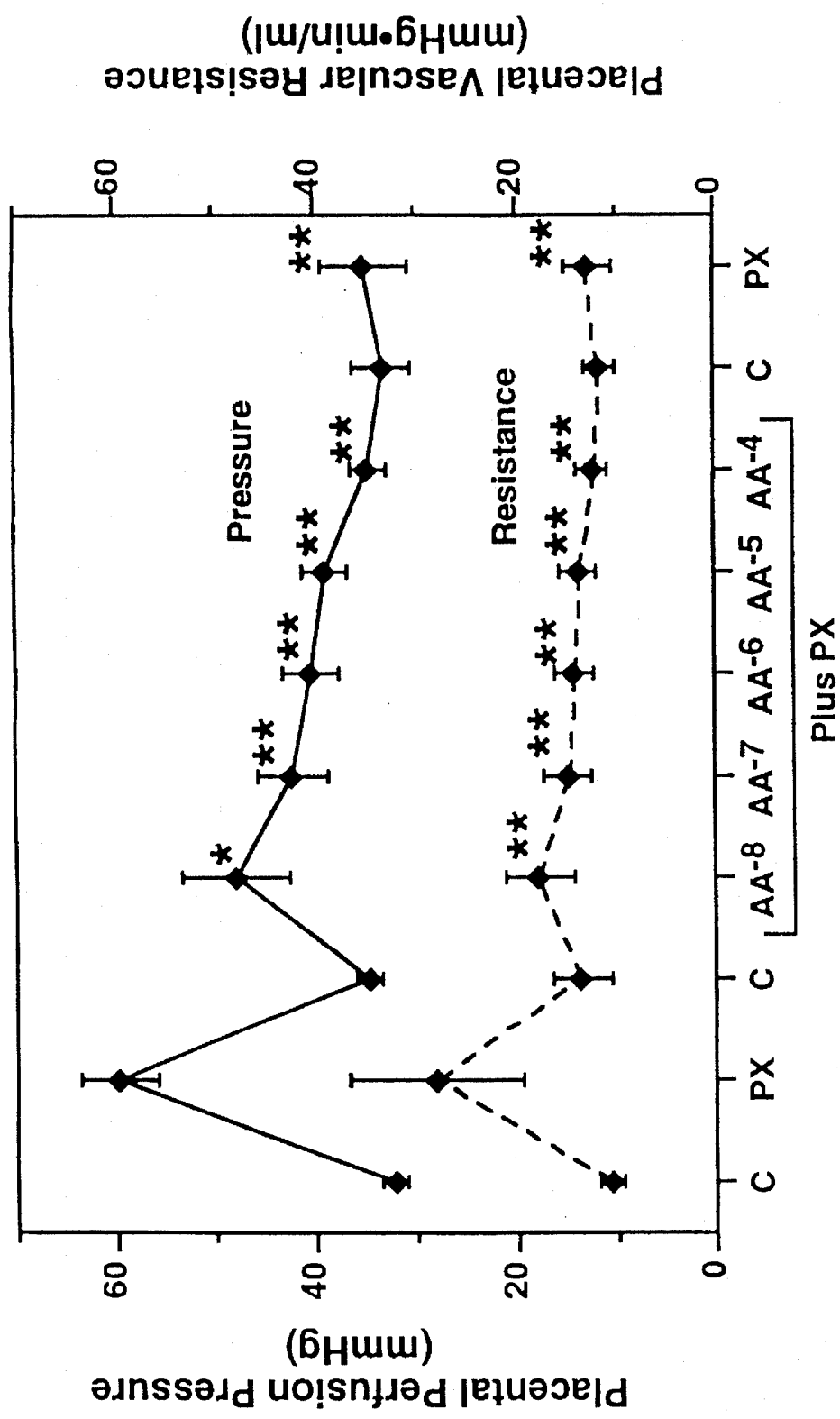
FIG. 2 shows a concentration-response curve demonstrating that the increase in perfusion pressure and vascular resistance induced by peroxide is inhibited in a concentration dependent manner by 7-(3,5,6-trimethyl-1,4-benzoquinon-2-yl)-7-phenylheptanoic acid.

FIG. 2 demonstrates that the increase in perfusion pressure and vascular resistance induced by peroxide is inhibited in a concentration dependent manner by 7-(3,5,6-trimethyl-1,4-benzoquinon-2-yl)-7-phenylheptanoic acid. Significant inhibition was achieved with a concentration as low as $1\times10^{-8}$ M. "C" represents the KRB buffer control perfusion. The asterisks indicate the values that are significantly lower than peroxide (PX) alone, * $P<0.05$, ** $P<0.01$.

Figure 3A:
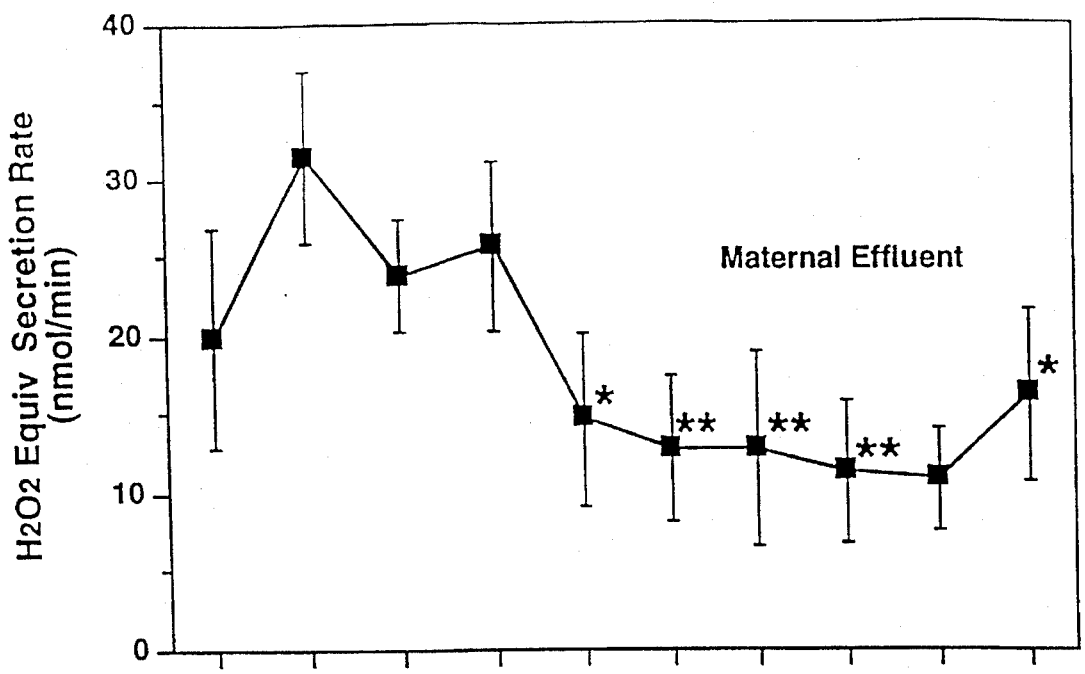
FIG. 3 shows, in plots of maternal and fetal effluent peroxide production rates versus concentration of 7-(3,5,6-trimethyl-1,4-benzoquinon-2-yl)-7-phenylheptanoic acid, the effect of peroxide and 7-(3,5,6-trimethyl-1,4-benzoquinon-2-yl)-7-phenylheptanoic acid on placental secretion (maternal and fetal effluents) of lipid peroxides.
Figure 3B:
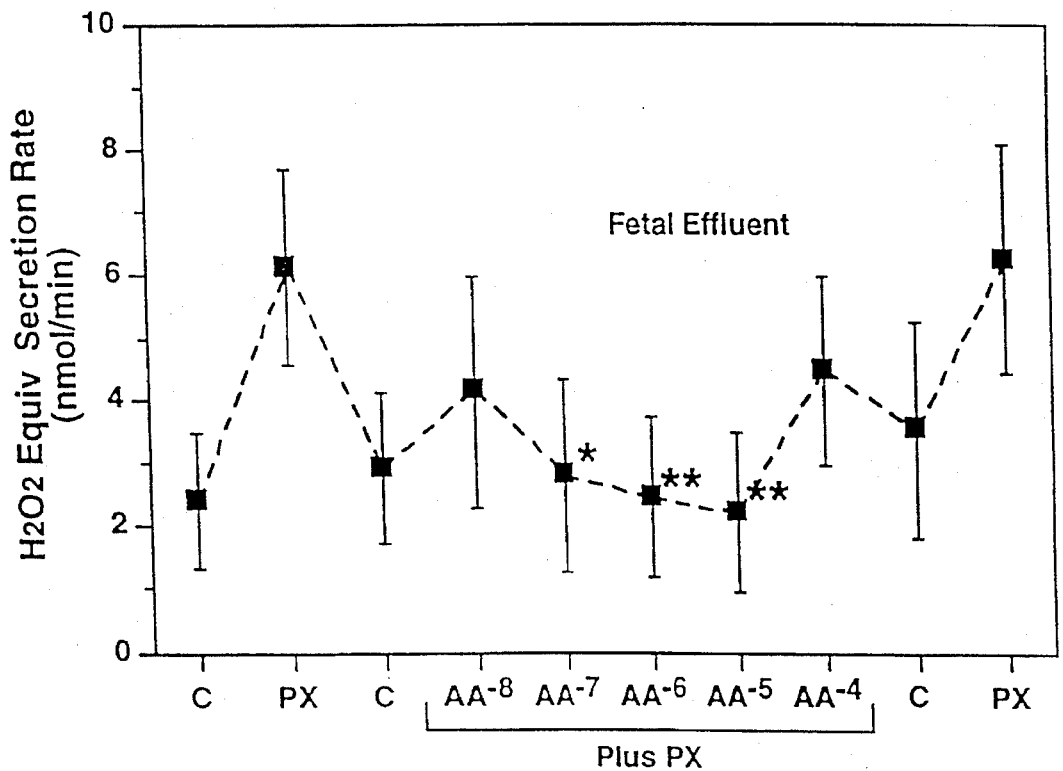

FIG. 3 shows the effects of peroxide (PX) and 7-(3,5,6-trimethyl-1,4-benzoquinon-2-yl)- 7-phenylheptanoic acid (AA) on placental secretion of lipid peroxides. Peroxide alone stimulated placental secretion of lipid peroxides into both maternal and fetal effluents, but this was inhibited by 7-(3,5,6-trimethyl-1,4-benzoquinon-2-yl)- 7-phenylheptanoic acid. Both maternal and fetal secretion rates were inhibited. The lack of an inhibitory effect on the fetal side at the highest concentration of 7-(3,5,6-trimethyl- 1,4-benzoquinon-2-yl)-7-phenylheptanoic acid ($10^{-4}$ M) may represent a nonspecific or toxic effect of the drug on the fetal placental vasculature at this high concentration.

Figure 4A:
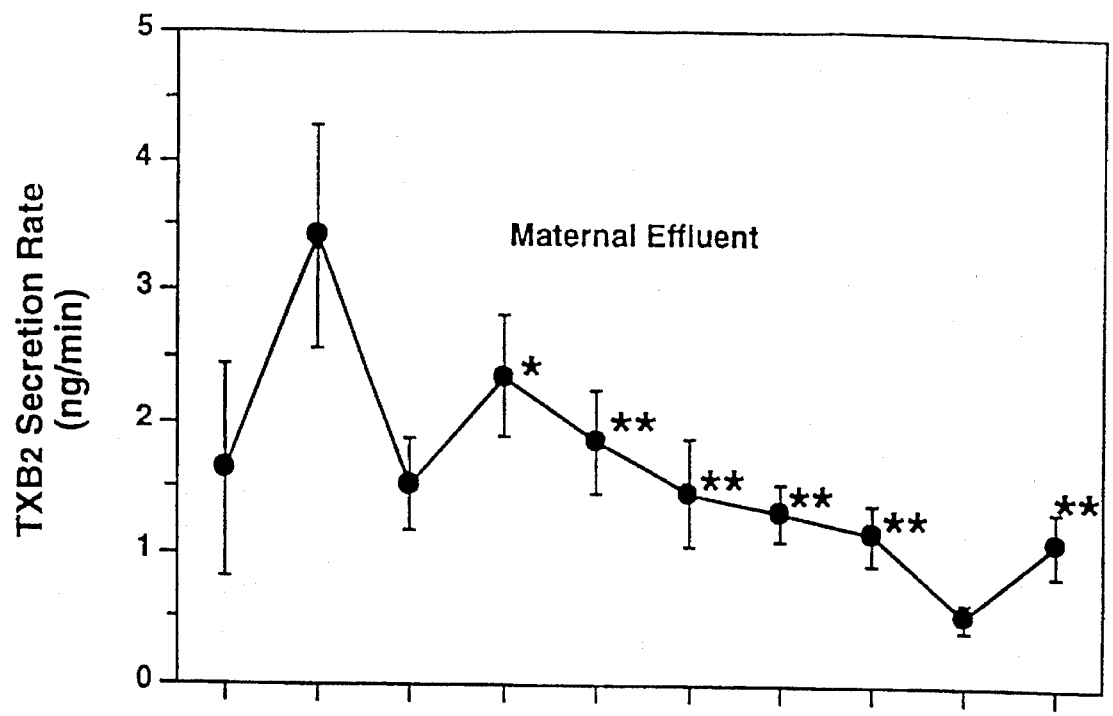
FIG. 4 shows, in plots of maternal and fetal effluent thromboxane production rates versus concentration of 7-(3, 5,6-trimethyl-1,4-benzoquinon-2-yl)-7-phenylheptanoic acid, the effects on placental secretion of thromboxane.
Figure 4B:
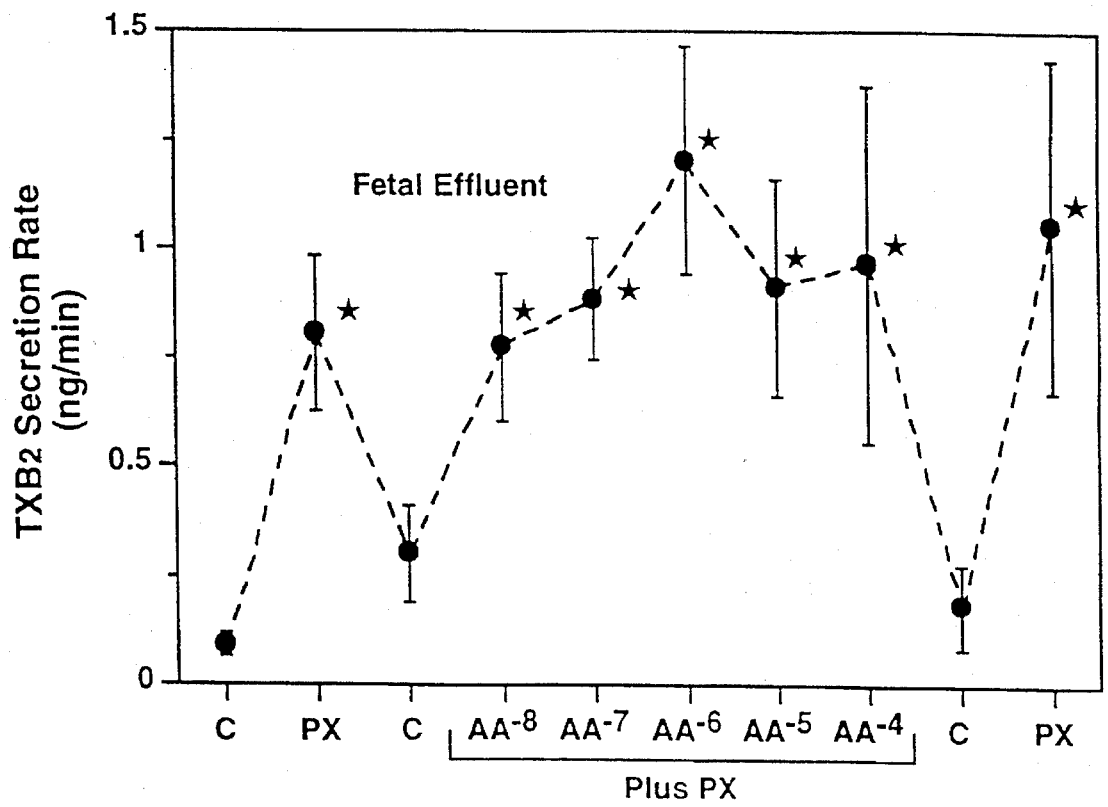

FIG. 4 shows the effects on placental secretion of thromboxane. Peroxide (PX) significantly increased thromboxane secretion on both sides of the placenta, but 7-(3,5,6-trimethyl-1,4-benzoquinon-2-yl)-7-phenylheptanoic acid (AA) only inhibited thromboxane secretion on the maternal side. The asterisks for the maternal effluent indicate the concentrations are significantly lower than PX alone, whereas the stars for the fetal effluent indicate the concentrations are significantly higher than the control perfusion, "C". This is a rather interesting finding with regard to the mechanism of action of 7- (3,5,6-trimethyl- 1,4-benzoquinon-2-yl)-7-phenylheptanoic acid on thromboxane. 7-(3,5,6-Trimethyl-1,4-benzoquinon-2-yl)-7-phenylheptanoic acid does not directly affect the PGH synthase enzyme, so the inhibitory effect on thromboxane on the maternal side is indirect, probably related to the decrease in lipid peroxides. PGH synthase requires a certain amount of peroxide tone for its activation. When the level of peroxide tone decreases, the activity of PGH synthase decreases which would result in a decrease in thromboxane production. The reason 7-(3,5,6-trimethyl-1,4-benzoquinon-2-yl)-7-phenylheptanoic acid did not inhibit thromboxane secretion on the fetal side of the placenta is not known, but it would not matter with respect to the overall effect of the compound. Because 7-(3,5,6-trimethyl-1,4-benzoquinon- 2-yl)-7-phenylheptanoic acid is a thromboxane receptor blocker, vasoconstriction is prevented despite the increase in fetal secretion of thromboxane (see FIG. 2).

Figure 5A:
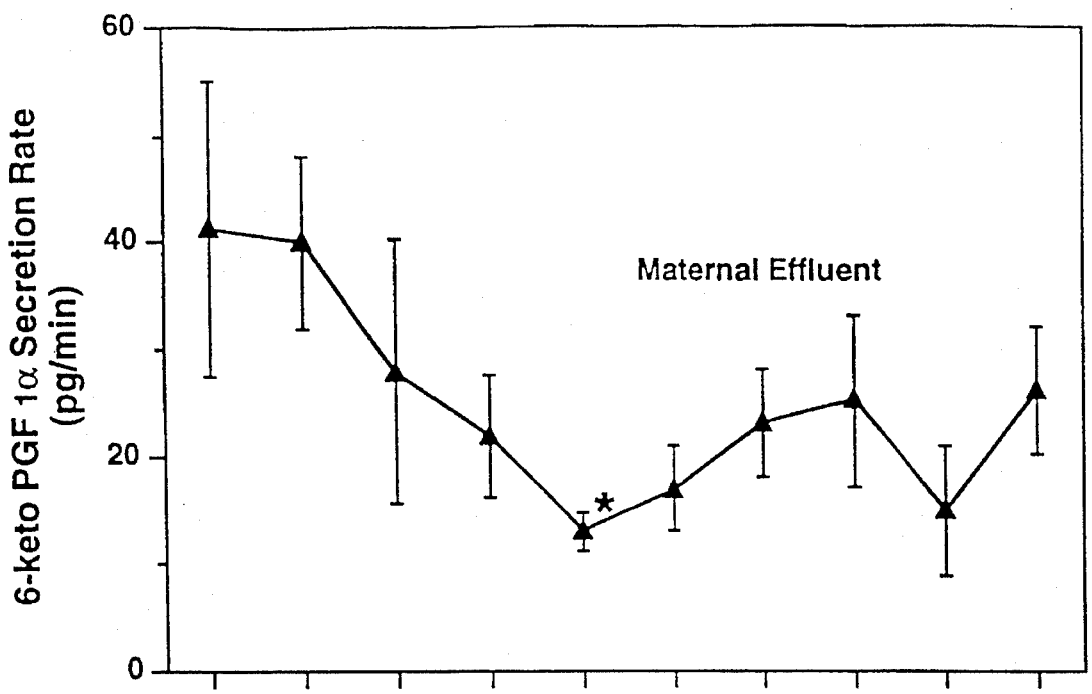
FIG. 5 shows, in plots of maternal and fetal effluent prostacyclin production rates versus concentration of 7-(3, 5,6-trimethyl-1,4-benzoquinon-2-yl)-7-phenylheptanoic acid, the effects on placental production of prostacyclin.
Figure 5B:
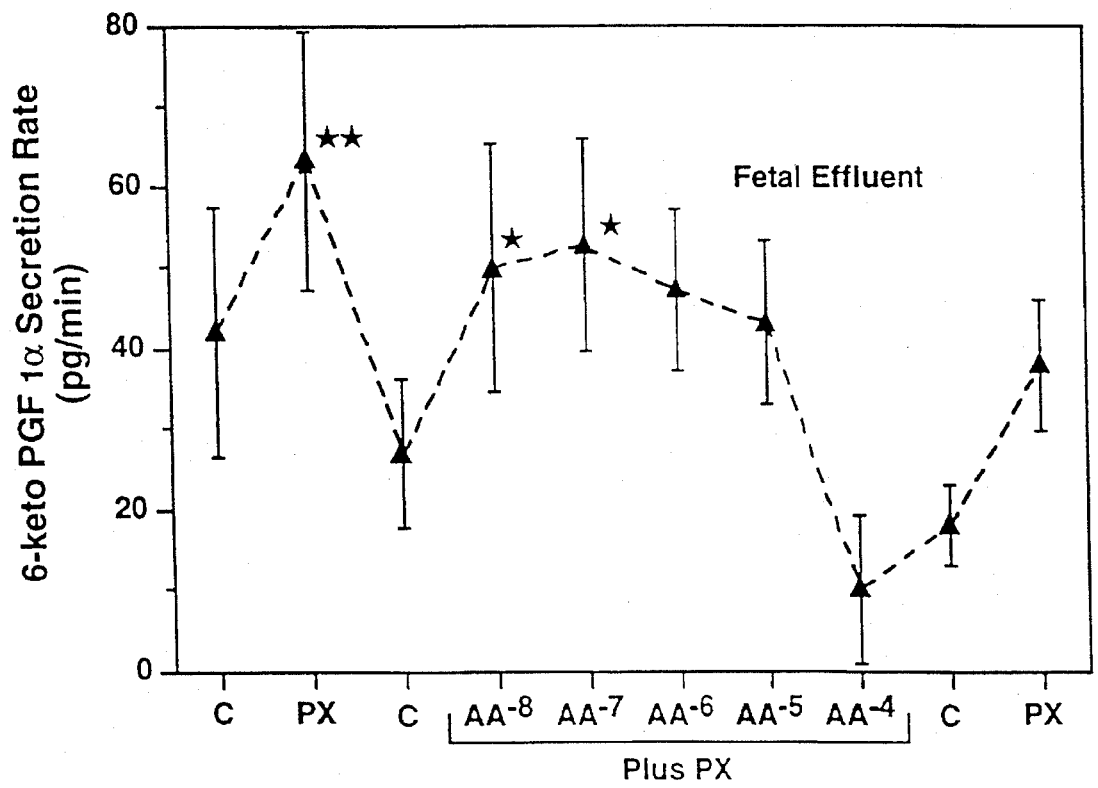
Figure 6:
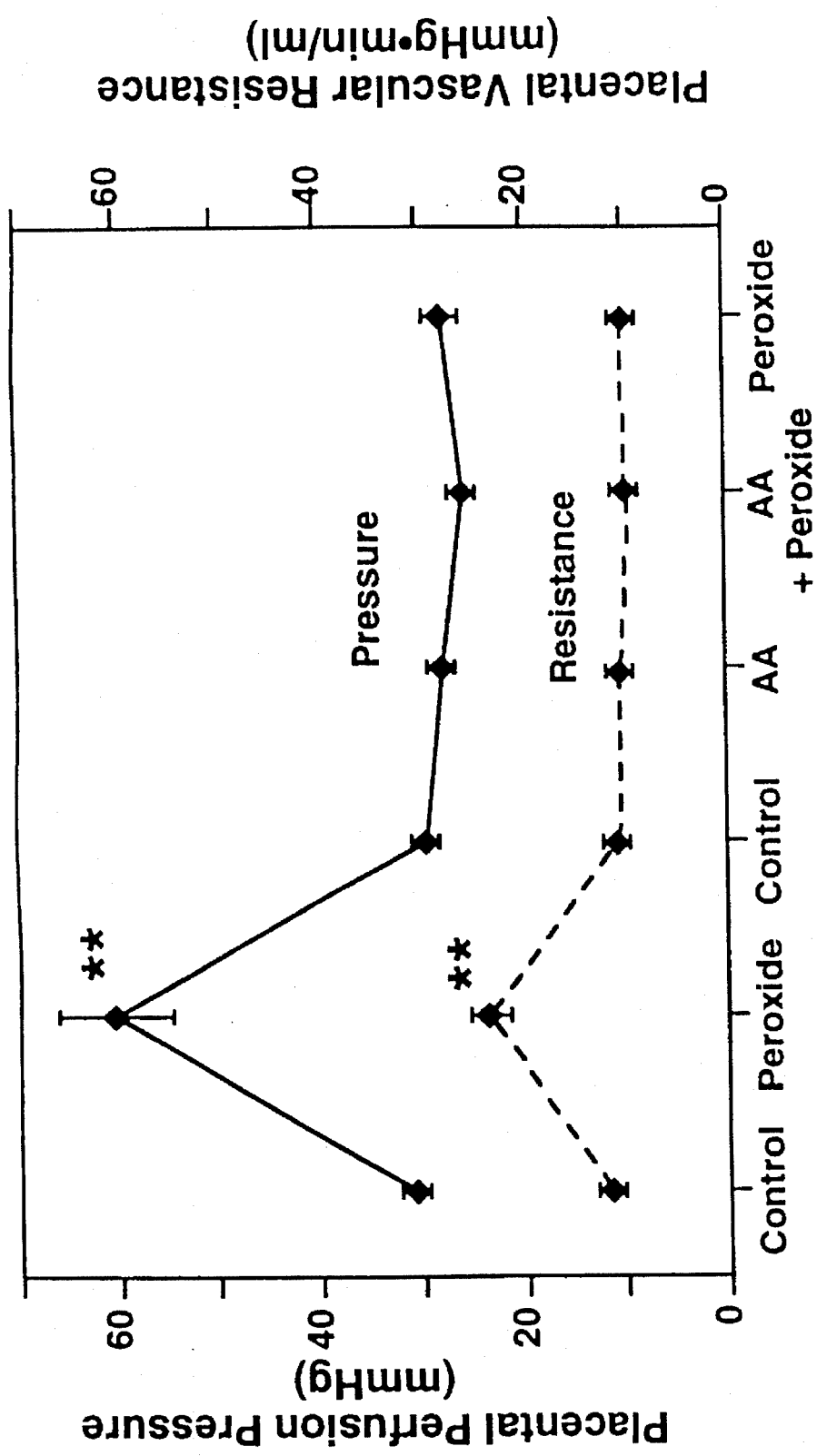
FIG. 6 shows a plot of the changes in perfusion pressure in the isolated human placental cotyledon in response to peroxide perfusion and perfusion of peroxide plus a single concentration of 7-(3,5,6-trimethyl-1,4-benzoquinon-2-yl)-7-phenylheptanoic acid.
Figure 7:
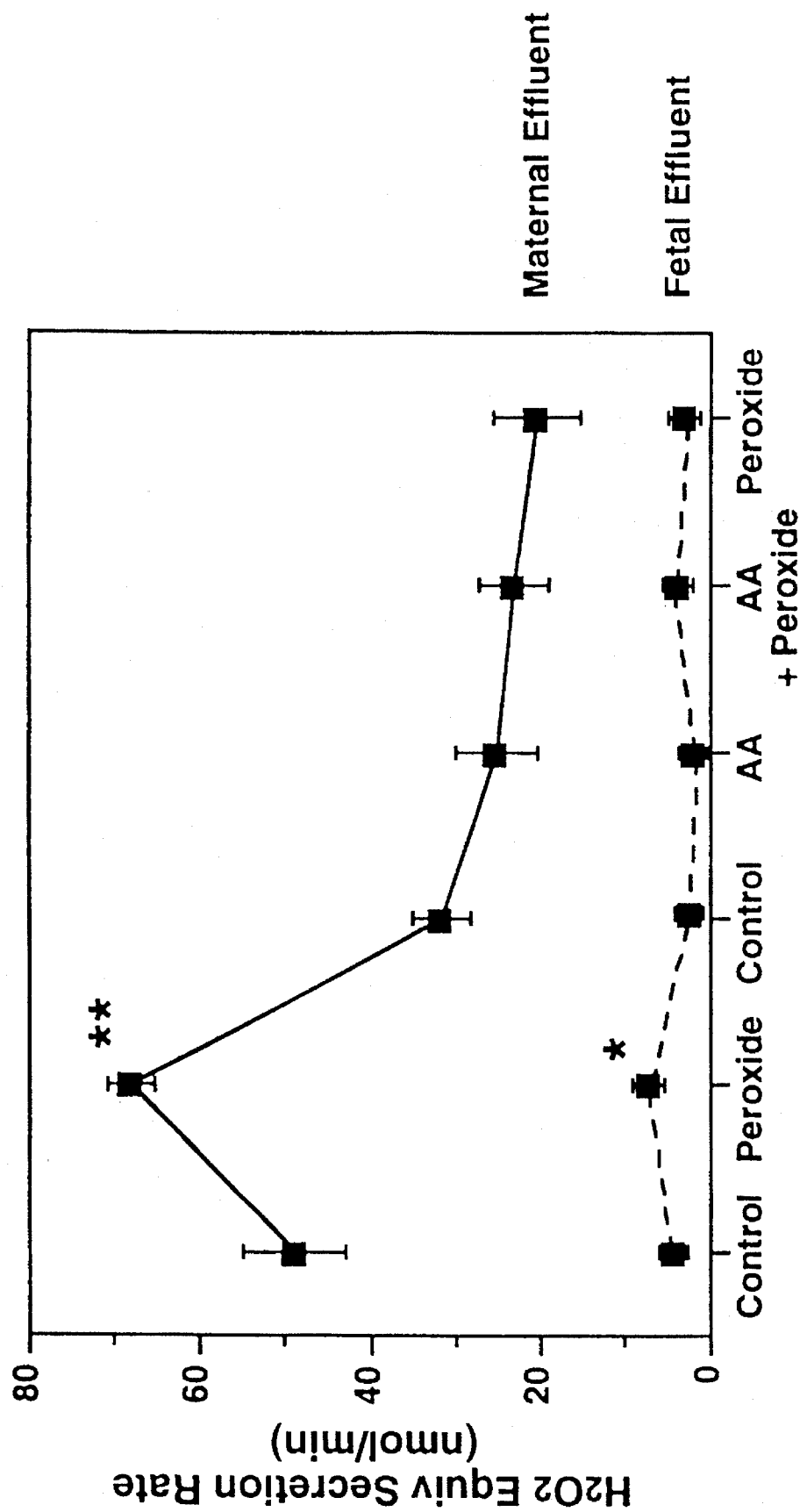
FIG. 7 shows, in plots of maternal and fetal effluent peroxide production rates versus a single concentration of 7-(3,5,6-trimethyl- 1,4-benzoquinon-2-yl)-7-phenylheptanoic acid, the effect of peroxide and 7-(3,5,6-trimethyl-1,4-benzoquinon-2-yl)-7-phenylheptanoic acid on placental production (maternal and fetal effluents) of lipid peroxides.
Figure 8:
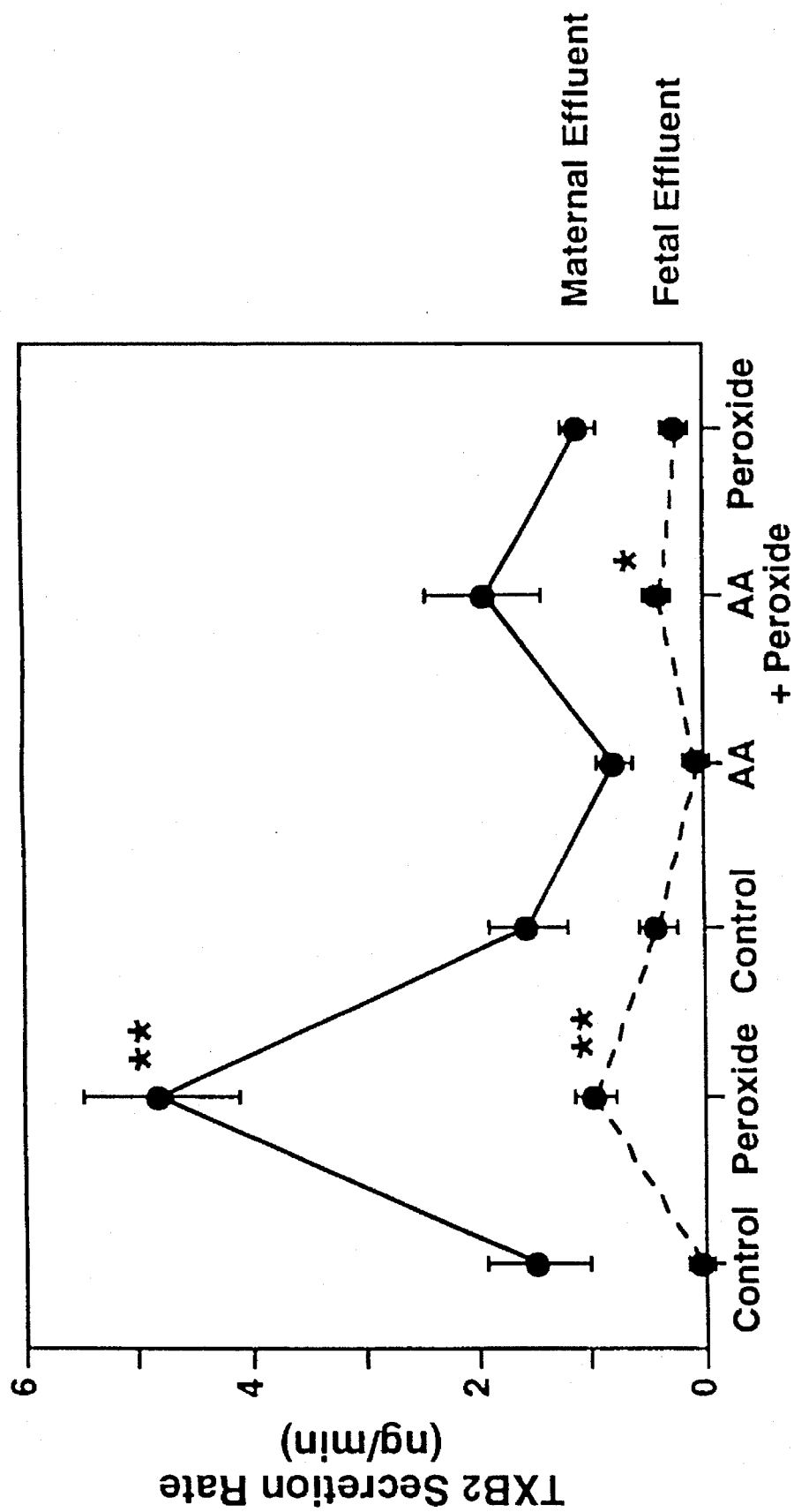
FIG. 8 shows, in plots of maternal and fetal effluent thromboxane production rates versus concentration of 7-(3, 5,6-trimethyl-1,4-benzoquinon-2-yl)-7-phenylheptanoic acid, the effects on placental production of thromboxane.
Figure 9:
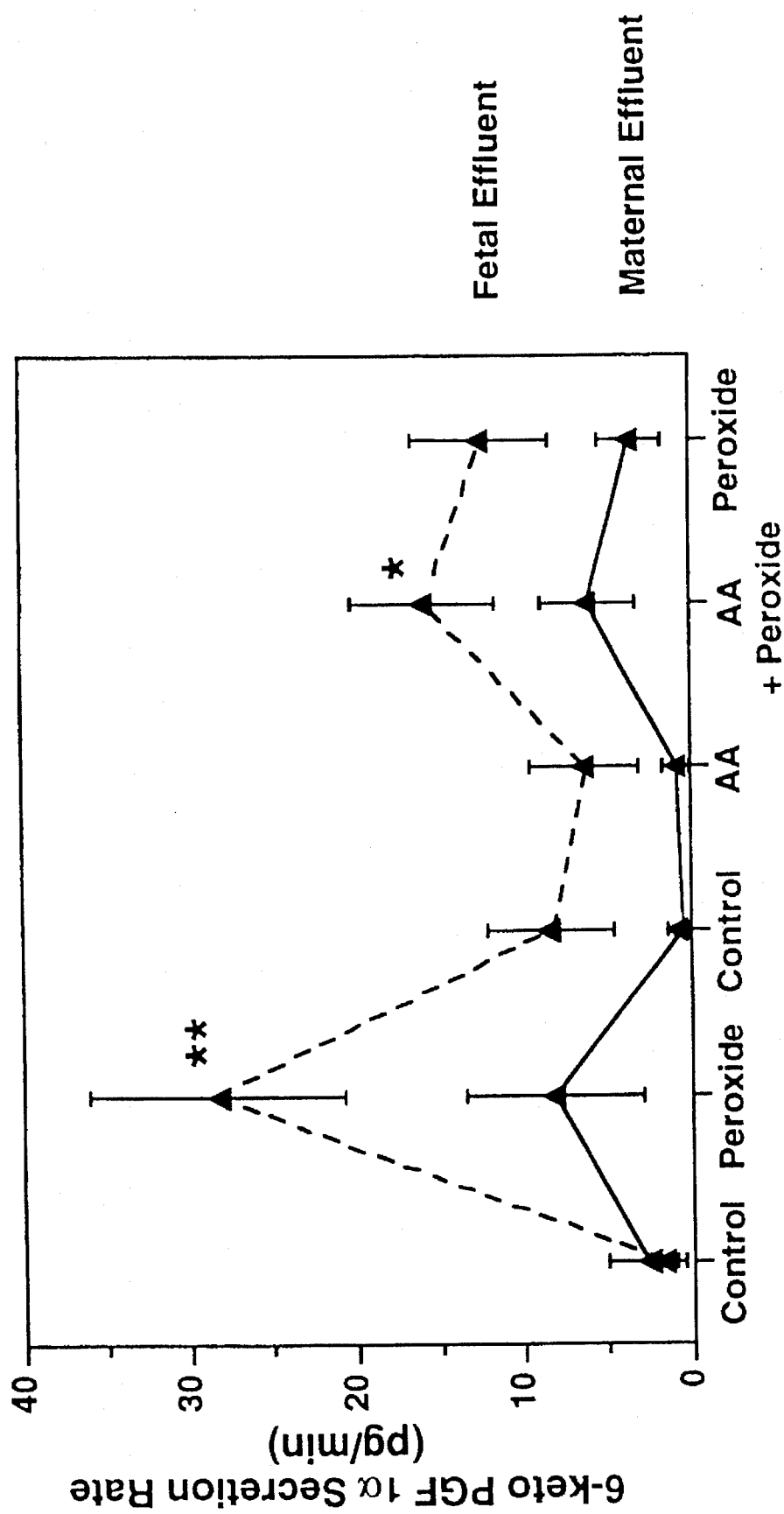
FIG. 9 shows, in plots of maternal and fetal effluent prostacyclin prtoduction rates versus a single concentration of 7-(3,5,6-trimethyl-1,4-benzoquinon-2-yl)-7-phenylheptanoic acid, the effects on placental production of prostacyclin.
Figure 10:
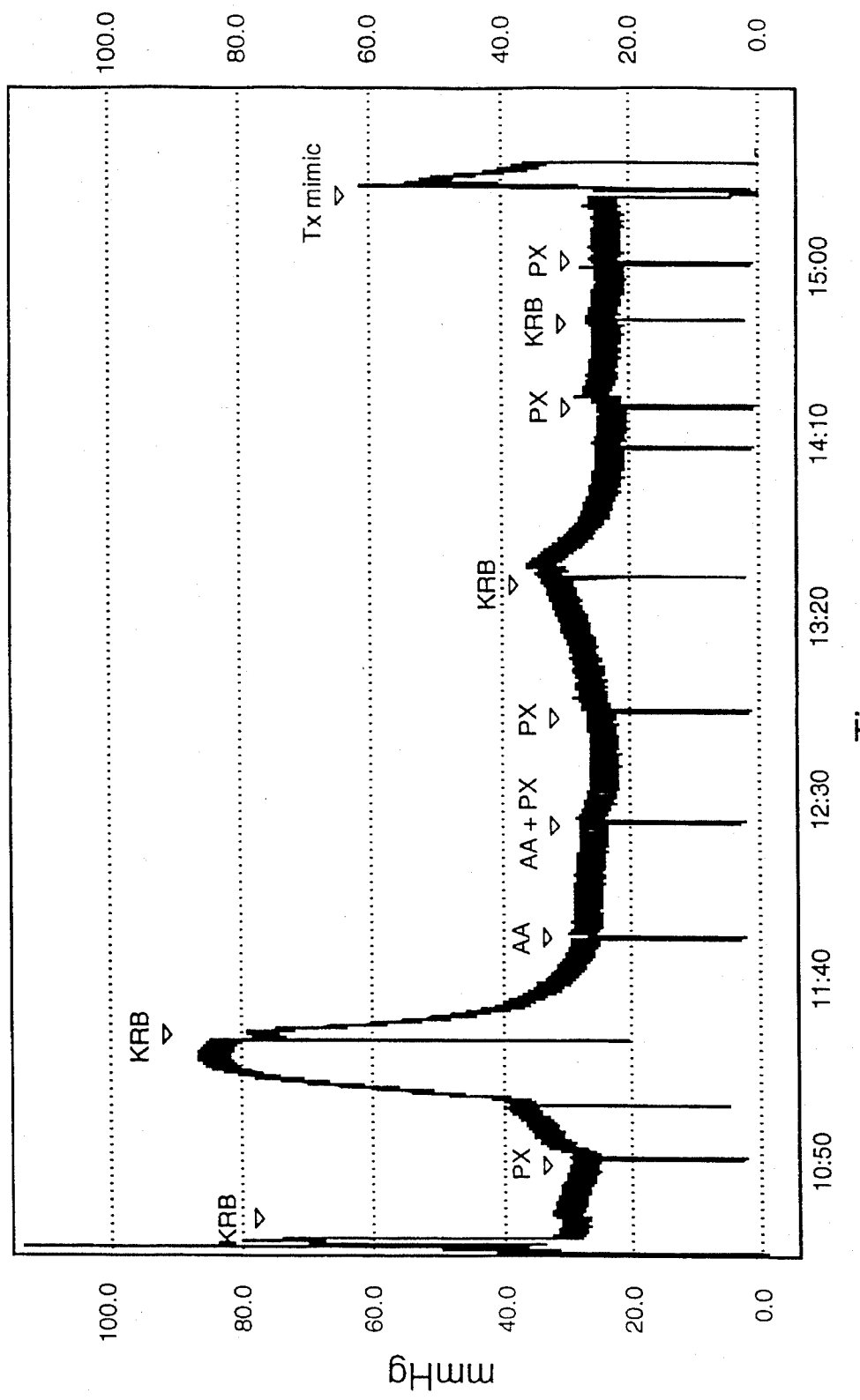
FIG. 10 shows a representative tracing of perfusion pressure in the isolated human placental cotyledon in which the placental cotyledon was continually challenged with peroxide perfusions.

FIG. 5 shows the effects on placental secretion of prostacyclin. The effects were similar to those of thromboxane, but not as clear cut statistically because of considerable variability in the secretion of prostacyclin's stable metabolite, 6-keto $PGF_1\alpha$.

EXAMPLE 2

Single Concentration of 7-(3,5,4-Trimethyl- 1,4-benzoquinon-2-yl)-7-phenylheptanoic Acid Placental cotyledons (n=6) were perfused serially for 20 minute intervals with the following treatments: Control KRB buffer, t-butyl hydroperoxide (100 μM) control KRB buffer, 7-(3,5,6-trimethyl-1,4-benzoquinon-2-yl)-7-phenylheptanoic acid ($1\times10^{-5}$ M), 7-(3,5,6-trimethyl-1,4-benzoquinon-2-yl)-7-phenylheptanoic acid plus t-butyl hydroperoxide (100 μM), and t-butyl hydroperoxide alone. Maternal and fetal effluent samples were collected and processed as described above for Example 1.

The results shown in FIGS. 6–9 are consistent with those obtained in Example 1. 7-(3,5,6-Trimethyl-1,4-benzoquinon-2-yl)-7-phenylheptanoic acid clearly prevents peroxide induced vasoconstriction and placental secretion of lipid peroxides demonstrating both its antioxidant and thromboxane receptor blocking effects. The differential effect of blocking maternal but not fetal secretion of thromboxane and prostacyclin is still evident. The lack of a blocking effect on the fetal side may actually be a favorable effect because the increase in prostacyclin would promote vasodilatation of the placental vasculature, while the vasoconstrictive effects of the increase in thromboxane would be blocked by the thromboxane receptor antagonist properties of the compound.

The antioxidant effect of 7-(3,5,6-trimethyl- 1,4-benzoquinon-2-yl)-7-phenylheptanoic acid persisted after its perfusion was discontinued, because the peroxide challenges did not increase lipid peroxide or thromboxane secretion.

Conclusions

The results of Examples 1 and 2 show that 7-(3,5,6-trimethyl-1,4-benzoquinon-2-yl)- 7-phenylheptanoic acid, a representative compound of the class of compounds having structural formula I above prevents peroxide induced vasoconstriction in the isolated perfused human placental cotyledon. It also blocks the ability of exogenous peroxide to increase placental secretion of lipid peroxides into the maternal and fetal effluents and of thromboxane into the maternal effluent. The antioxidant and thromboxane receptor blocking effects last at least for 2 hours and 20 minutes after perfusion with the compound is discontinued.

I claim:

1. A method for the therapy or prophylaxis of preeclampsia and eclampsia in pregnant females comprising administering to a patient in need of such treatment a therapeutically effective amount of a compound selected from the group consisting of compounds having the structural formula

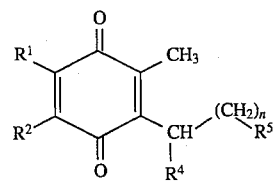

wherein
  n is an integer of from 2 to 10, inclusive;
  $R^1$ and $R^2$ are methyl; and
  $R^4$ is selected from the group consisting of
    unsubstituted phenyl, and
    phenyl substituted with one or more substituents selected from the group consisting of
      alkyl of one to three carbon atoms,
      alkoxy of one to three carbon atoms, and
      halogen;
  $R^5$ is selected from the group consisting of
    carboxyl
    alkoxycarbonyl of two to five carbon atoms, and
    phenoxycarbonyl;
or a pharmaceutically acceptable salt thereof.

2. The method of claim 1 wherein n is 6 or 7.

3. The method of claim 2 wherein said compound is selected from the group consisting of
  7-(3,5,6-trimethyl-1,4-benzoquinon-2-yl)-7-phenylheptanoic acid,
  6-(3,5,6-trimethyl-1,4-benzoquinon-2-yl)-6-(4-methoxyphenyl)hexanoic acid,
  7-(3,5,6-trimethyl-1,4-benzoquinon-2-yl)-7-(4-methoxyphenyl)heptanoic acid,
  7-(3,5,6-trimethyl-1,4-benzoquinon-2-yl)-7-(4-fluorophenyl)heptanoic acid, and
  7-(3,5,6-trimethyl-1,4-benzoquinon-2-yl)-7-(4-methylphenyl)heptanoic acid;
or a pharmaceutically acceptable salt thereof.

4. A method for the therapy or prophylaxis of preeclampsia and eclampsia in a pregnant female woman comprising administering to a patient in need of such treatment a therapeutically effective amount of 7-(3,5,6-trimethyl-1,4-benzoquinon-2-yl)-7-phenylheptanoic acid or a pharmaceutically acceptable salt thereof.

* * * * *